(12) United States Patent
Fritsch

(10) Patent No.: US 8,595,881 B2
(45) Date of Patent: Dec. 3, 2013

(54) ELECTRIC APPLIANCE FOR PERSONAL USE

(75) Inventor: Thomas Fritsch, Eppstein (DE)

(73) Assignee: Braun GmbH, Kronberg (DE)

( * ) Notice: Subject to any disclaimer, the term of this patent is extended or adjusted under 35 U.S.C. 154(b) by 207 days.

(21) Appl. No.: 13/183,745

(22) Filed: Jul. 15, 2011

(65) Prior Publication Data

US 2012/0011666 A1  Jan. 19, 2012

(30) Foreign Application Priority Data

Jul. 17, 2010 (EP) .................................... 10007425

(51) Int. Cl.
*A46B 13/02* (2006.01)
(52) U.S. Cl.
USPC .......................................... 15/22.1; 16/111.1
(58) Field of Classification Search
USPC ............................ 15/22.1, 22.2, 23; 16/111.1
See application file for complete search history.

(56) References Cited

U.S. PATENT DOCUMENTS

| 5,707,166 A | 1/1998 | Jeannet et al. |
| 6,422,867 B2 | 7/2002 | Lang et al. |
| 2004/0007244 A1 | 1/2004 | Harms |

OTHER PUBLICATIONS

International Search Report for PCTRB2O11/053166 dated Oct. 25, 2011.

*Primary Examiner* — Shay Karls
(74) *Attorney, Agent, or Firm* — John P. Colbert

(57) ABSTRACT

A handle of an electrical appliance for personal use is disclosed. The handle includes an elongated housing for receiving functional components of the appliance; and a control unit or an electric power supply. The housing includes at least two tube-shaped housing parts connected to each other at end portions thereof. An annular sealing element is associated with the end portions to seal the interface between the housing parts. The end portions of the housing parts have substantially the same diameter such that end surfaces of the housing parts abut against each other or against the annular sealing element. A holding member extending over the interface between the housing parts and the sealing element is provided for holding the housing parts together.

12 Claims, 7 Drawing Sheets

ELECTRIC APPLIANCE FOR PERSONAL USE

CROSS REFERENCE TO RELATED APPLICATION

This application claims the benefit of European Patent Convention Application No. 10007425.1, filed Jul. 17, 2010, the substance of which is incorporated herein by reference in its entirety.

FIELD OF THE INVENTION

The present disclosure relates to electrical appliances for personal use, which in particular may be an electrical toothbrush. More particularly, the present disclosure relates to a handle of such an electrical appliance.

BACKGROUND OF THE INVENTION

Handles of small-scale electrical appliances such as toothbrushes or shavers usually fulfil a double function. On the one hand, the handle forms the grip at which the appliance is gripped by a user's hand to control the orientation and to move the working tool of the appliance such as the brush head over the teeth. On the other hand, the handle usually receives at least a part of the drive unit for driving the working tool of the appliance, wherein often an electric motor, the batteries for powering the motor, a transmission for transmitting the motor's rotation to the working tool and a control unit are received in the handle.

The minimum size of the handle is therefore determined by the size of the drive unit and the space required for receiving the drive unit. Consequently, in order to reduce the size of the handle and to reduce the diameter thereof, it has been tried to reduce the size of the drive unit to achieve good handling and nice ergonomic appreciation of the handle. On the other hand, as the size reduction of the drive unit is expensive and still limiting, it is desirable to make the housing surrounding the drive unit as slim as possible for a given size of the drive unit. In order to achieve this, an intelligent design of the housing is necessary so as to utilize the interior space of the housing as far as possible to accommodate the drive unit's components.

Prior art toothbrushes usually have a handle forming a tube-shaped housing consisting of two or more housing parts which are connected at end portions thereof. In order to achieve a waterproof or water-resistant sealing of the interface of the housing parts, the housing parts are designed to overlap each other so that the end portion of a first housing part having a smaller diameter can be inserted into the end portion of the other housing part having a larger diameter. The overlapping end portions may be provided with threads so that the housing parts can be connected to each other by means of screwing them together. Such screw-type connection between the housing parts allows for easy sealing the housing part's interface in a waterproof manner, as an elastic sealing ring can be placed between the housing parts and press against step-shaped contours to achieve sealing contact of the elastic sealing ring to the housing parts.

Such screw-type connection of the housing parts with end portions of the housing parts being inserted into each other increases the outer circumferential dimensions of the housing since the overlapping end portions inserted into each other double the wall thickness and provide for a stepped contour of the interior space, thus wasting a part of the interior space.

It is also known to give the end portions of housing parts the same diameter and to connect the two end portions with end surfaces lying onto each other, thereby forming a butt joint of the housing parts. For example, document US 2007-0217199 shows a light-based dermal treatment apparatus comprising an outer shell consisting of two substantially tubular shell parts having end surface butting against each other. However, such known housing configuration is difficult in terms of sealing the housing parts and making the housing waterproof. US 2007-0217199 therefore suggests to connect the two housing parts by means of welding the parts together or using adhesive to glue the housing part together. Such connection, however, is of course disadvantageous since it is no longer possible to open the housing so as to, for example, change the batteries. Moreover, to bring the two housing parts into alignment with each other and to position the end surfaces onto each other, the document suggests to additionally use an inner shell forming a second interior housing what contravenes the desire to reduce the outer dimensions of the housing as far as possible for a drive unit of a given size to be received in the housing.

It is a desire to provide an improved handle of an electrical appliance for personal use, which avoids disadvantages of the prior art and in particular provides further improvements thereof. In particular, it is desired to provide maximum interior space in both housing parts without sacrificing waterproof sealing that can be opened easily.

SUMMARY OF THE INVENTION

In one embodiment, a handle of an electrical appliance for personal use is provided. The handle includes an elongated housing for receiving functional components of the appliance; and a control unit or an electric power supply. The housing includes at least two tube-shaped housing parts connected to each other at end portions thereof. An annular sealing element is associated with the end portions to seal the interface between the housing parts. The end portions of the housing parts have substantially the same diameter such that end surfaces of the housing parts abut against each other or against the annular sealing element. A holding member extending over the interface between the housing parts and the sealing element is provided for holding the housing parts together.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

DETAILED DESCRIPTION OF THE INVENTION

Figure 1:
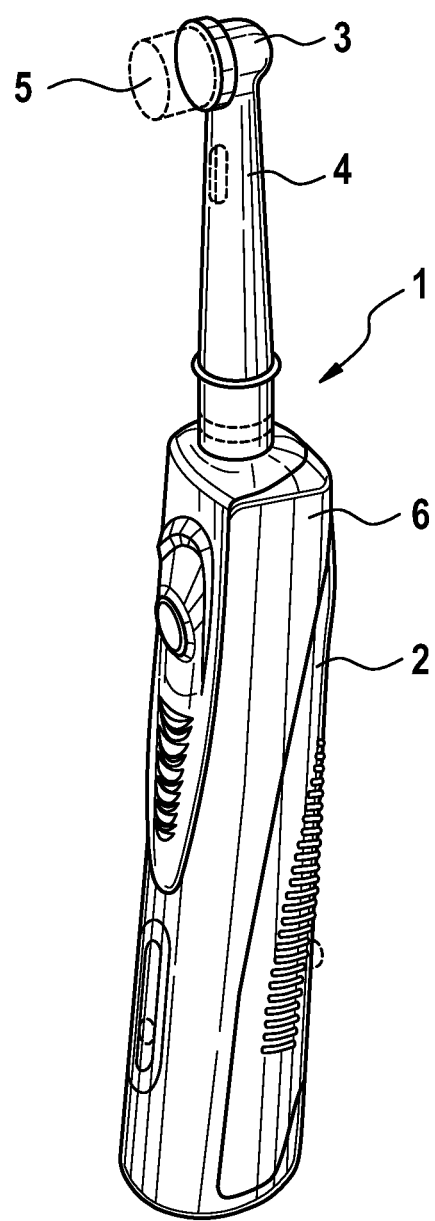
FIG. 1: a perspective view of an exemplary electric toothbrush according to one or more embodiments illustrated and described herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

In one embodiment, in order to combine maximum space in both housing parts with a waterproof connection that can be operated easily, a butt joint is provided between the housing parts which are held together by a mechanical holding member. The end portions of the housing parts do not overlap each other so that both housing parts can have the minimum inner diameter necessary to accommodate the drive unit's components received in the housing, thus resulting in a minimum outer dimension of the housing. In accordance with one embodiment, the end portions of the housing parts have substantially the same diameter such that end surfaces of the housing parts butt against each other or against the annular sealing element, wherein a holding member extending over the interface between the housing parts and the sealing element is provided for holding said housing parts together. In particular, the housing has an inner circumferential surface with a continuous contour going smoothly over the interface from one housing part to the other housing part without steps or other changes in the inner diameter. More particularly, the housing parts' portions neighbouring the interface between the housing parts may define a substantially cylindrical contour bridging the interface between the housing parts.

Consequently, the maximum space is available in both housing parts with both housing parts having minimum dimensions including inner diameter for a given size of the components to be received in the housing. Since the housing parts are not inserted into each other, the length of the entire housing basically corresponds to the sum of the length of the housing parts, and optionally, depending on the arrangement of the sealing element, the sealing element's thickness. The wall thickness of the housing basically corresponds to each of the housing parts' wall thickness even in the zone of the interface.

In accordance with an embodiment, the mechanical holding member holding together the neighbouring housing parts is a separate part not integrally formed with any of the housing parts so it is separately mounted and can be separately manufactured from a material different from the housing parts' material and/or best for giving the holding member the desired properties such as increased strength and/or flexibility with minimum thickness. For example, the holding member can be made of a metal material such as steel, whereas in particular the housing parts are made of plastic, for example, a hard plastic and/or a combination of different plastics such as hard plastic and soft plastic.

In one example, in order to reduce the number of parts inside the housing and to provide maximum space for the functional components of the appliance to be received in the housing, the holding member may fulfil a double function. In addition to holding the housing parts together, the holding member may be adapted to position and/or hold and/or mount at least one of said functional components such as the electric motor and/or the transmission and/or the power supply for the motor and/or the control unit. More particularly, the holding member may be a part of the chassis which is used to pre-mount the drive unit's components which is then together with the components inserted in the housing. More particularly, the holding member may be provided with support means for supporting at least one of the functional components to be received inside the housing.

In addition to such chassis or mounting function, the holding member may be provided with support means for supporting the sealing element which seals the interface between the housing parts in a water-resistant manner. More particularly, the holding member may be provided with an annular support surface for supporting an inner circumferential surface of the sealing element to prevent the sealing element from bulging inwardly and/or for making sure that the sealing member is appropriately pressed against or in contact to the end portions of the neighbouring housing parts. In one embodiment, the sealing element is made from a soft, deformable material which is self-adapting its contour to the contour of the respective housing part to achieve a waterproof and/or gas-proof connection irrespective of tolerances in shape and dimension of the housing parts and/or the sealing element. In one embodiment, the sealing element is made from an elastic material such as rubber, wherein the sealing element is in particular ring-shaped.

The sealing element may be arranged between the two housing parts in different ways. In accordance with an embodiment, the annular sealing element may be positioned between the ring-shaped end surfaces of the housing parts butting against each other or more precisely, butting against the sealing element positioned therebetween. In this embodiment, the sealing element basically has the same diameter and the same ring shape as the end surfaces of the housing parts so that the sealing element is sandwiched between the two housing parts. In other words, in the axial direction parallel to the longitudinal axis of the housing, a first housing part is followed by the sealing element which in turn is followed by the second housing part. Such arrangement of the sealing element provides for maximum interior space in the housing with no diameter reduction in the zone of the interface between the housing parts.

When such arrangement of the sealing element is chosen, the holding member is in particular adapted to be a tensioning member for tensioning the two housing parts onto each other in the axial direction parallel to the longitudinal axis of the housing. Such axial tension provided by the holding member applies pressurizing force acting from both housing parts onto the sealing element positioned therebetween and ensures the necessary contact pressure of the sealing element onto each of the housing parts.

In the alternative to such arrangement of the sealing element between the end surfaces opposite to each other, the sealing element may be positioned radially inside of the housing parts and/or on the inner circumferential side of the housing so that the interface between the two housing parts is sealed in a waterproof manner on the inside of the housing. In another embodiment, the sealing element may have an outwardly projecting, in particular annular sealing lip which is in sealing contact with the inner circumferential surface of the housing.

According to one embodiment, the sealing element may extend over the interface to be in contact with the end portions of both neighbouring housing parts. For example, the sealing element may have two outwardly projecting, annular sealing lips which are spaced from each other in the longitudinal direction of the housing, wherein one of said sealing projections is in contact with a first one of the housing parts, whereas a second sealing projection is in contact with the inner circumferential side of a second one of the housing parts. Consequently, the sealing element may bridge the interface of the two housing parts on an inner circumferential side thereof. With such arrangement of the sealing element, the end surfaces of the housing parts may be in contact directly with each other.

In the alternative or in addition to such bridging sealing element, a plurality of separate sealing elements may be provided with the holding element being used as a part of the sealing device to connect the separate sealing elements. In another embodiment, a first sealing element may be provided on the inner circumference of a first housing part, whereas a second sealing element is provided on the inner circumference of the second housing part, wherein both sealing elements are in particular ring-shaped and/or in sealing contact with the inner circumferential side of the respective housing part. So as to achieve waterproof sealing of the interface of the two housing parts between the two sealing elements, the holding member may be provided with a sleeve portion bridging the interface and in sealing contact with both sealing elements. For example, the sealing elements are accommodated within ring-shaped clearances between the inner circumferential side of the housing and the outer circumferential surface of the sleeve portion such that the respective outer circumferential surface portions of the sleeve press the sealing element radially outward onto the housing.

In accordance with an embodiment, the at least one sealing element may be accommodated within an annular, in particular groove-shaped recess which may be provided in the inner circumference of the respective housing part. However, a particular annular recess is provided in the outer circumference of the holding member, in particular the sleeve portion of said holding member. When the sealing element is provided on the inside of the housing, it may be desired to have the interface and/or the sealing element positioned in a zone where the functional components to be received in the housing need less radial space and/or have a reduced diameter. In particular, the interface and/or the sealing element may be positioned where the electric motor is connected to the electric power storage such as batteries and/or in a zone in-between the electric motor and the electric accumulator. In such zone the drive unit received in the housing has usually a reduced diameter.

In one embodiment, the holding member may hold the housing parts together in different ways. For example, there is a form-fitting engagement of the holding member with the housing parts to ensure sufficient strength of the fixture. More particularly, the holding member is provided with form-fitting engagement means for engaging at least one of the housing parts at an inner circumferential side thereof, wherein said inner circumferential side of the respective housing part has complementary form-fitting engagement means to engage said engagement means of the holding member.

So as to combine easy locking of the holding member to the respective housing part with minimum space required for the locking device, the form-fitting engagement means of the holding member and of the housing part may include an elastic latching element adapted to elastically move in a direction transverse to the longitudinal axis of the housing, wherein the elastic transverse movement of the latching element is in particular automatically effected when moving the holding member and the housing part relative to each other in the longitudinal direction, thus locking the holding member to the housing part automatically when pushing the holding element into the housing part in the longitudinal direction.

For example, the latching element may elastically move radially when reaching the position of engagement, wherein in particular the latching element and/or the complementary locking element may have a ramp surface to bring the latching element into an elastically deformed position before said position of engagement is reached. After further movement of the holding member relative to the housing part in the longitudinal direction and when reaching the locking position, the ramp surface gets out of engagement so that the latching element may elastically return into its locking position providing locking engagement of the holding member with the housing part.

In accordance with one embodiment, the respective housing part may be provided with an undercut recess at an inner circumferential surface thereof, wherein the holding element is provided with an elastic tongue having an undercut projection adapted to cooperate with the recess and/or having a shape fitting into the recess to provide locking engagement. In the alternative, the recess may be provided on the elastic tongue, whereas the projection can be provided at the housing part. For example, the housing part may be provided with an inwardly projecting hook whereas the elastic tongue may have a through-hole for receiving said hook. However, it may be desired to have an in particular groove-shaped recess in the inner circumference of the housing part and to have an outwardly projecting engagement hook on the elastic tongue of the holding element.

The electrical appliance for personal use which is shown in FIG. 1, is an electric toothbrush 1 which includes a brush head 3 which is provided with an elongated, substantially tube-shaped neck 4 which is releasably connected to handle 2. The brush head 3 may include a bristle carrier provided with a plurality of tufts of bristles or other tooth-cleaning or oral care tools such as interdental pins or bar-shaped plastic bodies. The bristle carrier may be oscillated in a rotatable manner about an axis perpendicular to the longitudinal axis 17 of the toothbrush 1.

In one embodiment, the handle 2 includes an elongated housing 6 extending along said longitudinal axis 17 of the handle 2 and forms a body to be gripped by a user's hand. The handle 2 includes an electric power source or power supply 9 such as batteries or an accumulator, and furthermore an electric motor 7 powered by said power source 9 and a control unit including a circuit board 8 and a start/stop button for controlling the drive unit. All these functional components of the drive unit of the toothbrush 1 are received in the interior of the housing 6 of the handle 2, as shown, for example, in FIG. 5 or FIG. 7, wherein the electric motor 7 and the accumulator of the power source 9 are positioned one behind the other along said longitudinal axis 17, whereas the control unit 8 may be positioned along the circumferential side of one of the other components such as the electric motor, as will be described in detail below.

Figure 6:
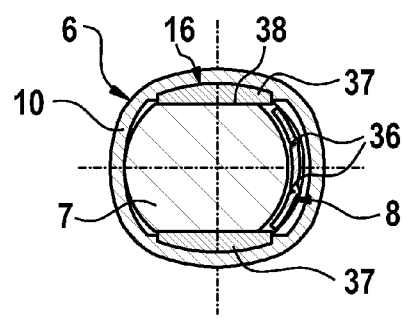
FIG. 6: is a cross-section of the handle along line A-A in FIG. 5, wherein the holding element formed by the chassis is shown to extend along opposite sides of the motor and wherein a printed circuit board of the control unit is shown to have a curved contour in this position in a circumferential gap between the motor and the housing.
Figure 8:
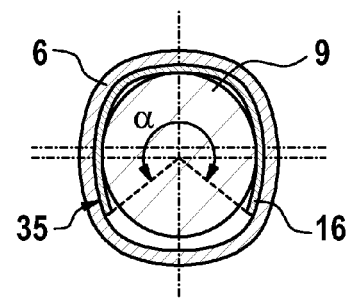
FIG. 8: a cross-sectional view of the handle along line B-B in FIG. 7, wherein the holding member formed by the chassis provides for accommodation of the accumulator.
Figure 10:
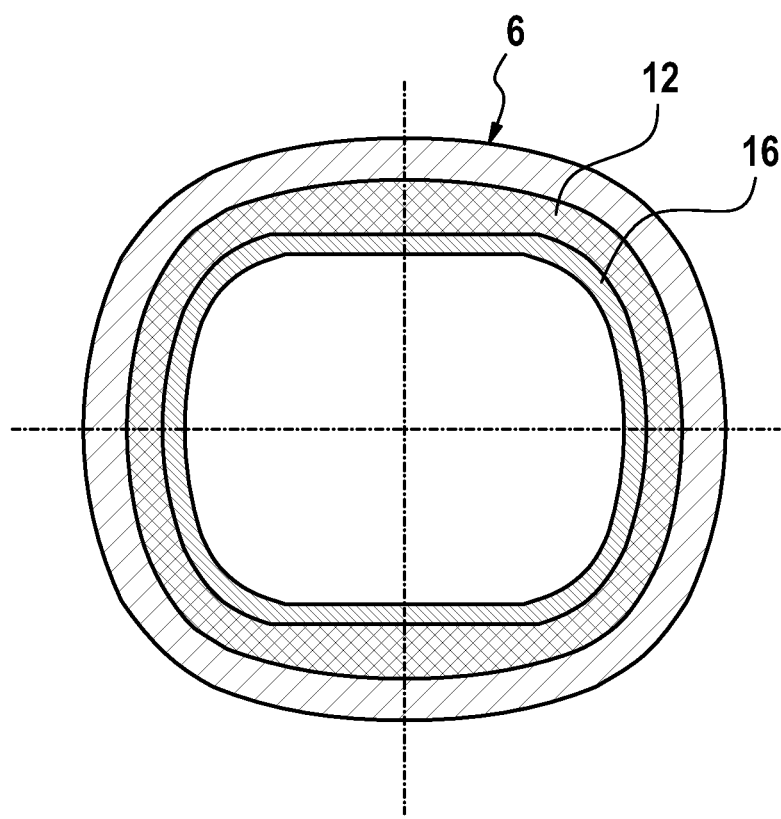
FIG. 10: a cross-sectional view of the handle along line C-C in FIG. 9.

The housing 6 of the handle 2 may include two separate housing parts 10 and 11 which are connected to each other to form together the housing 6. Each of said housing parts 10 and 11 has an elongated, substantially cylindrical shape with a cross-sectional contour that can be substantially circular, at least at the end portions 10a and 11a of the housing parts 10 and 11 where said housing parts 10 and 11 are connected to each other. However, the cross-section of the housing parts 10 and 11 is not necessarily circular, but also may have flattened sectors or sides to become oval or elliptical as shown in FIG. 6, 8 or 10.

Figure 2:
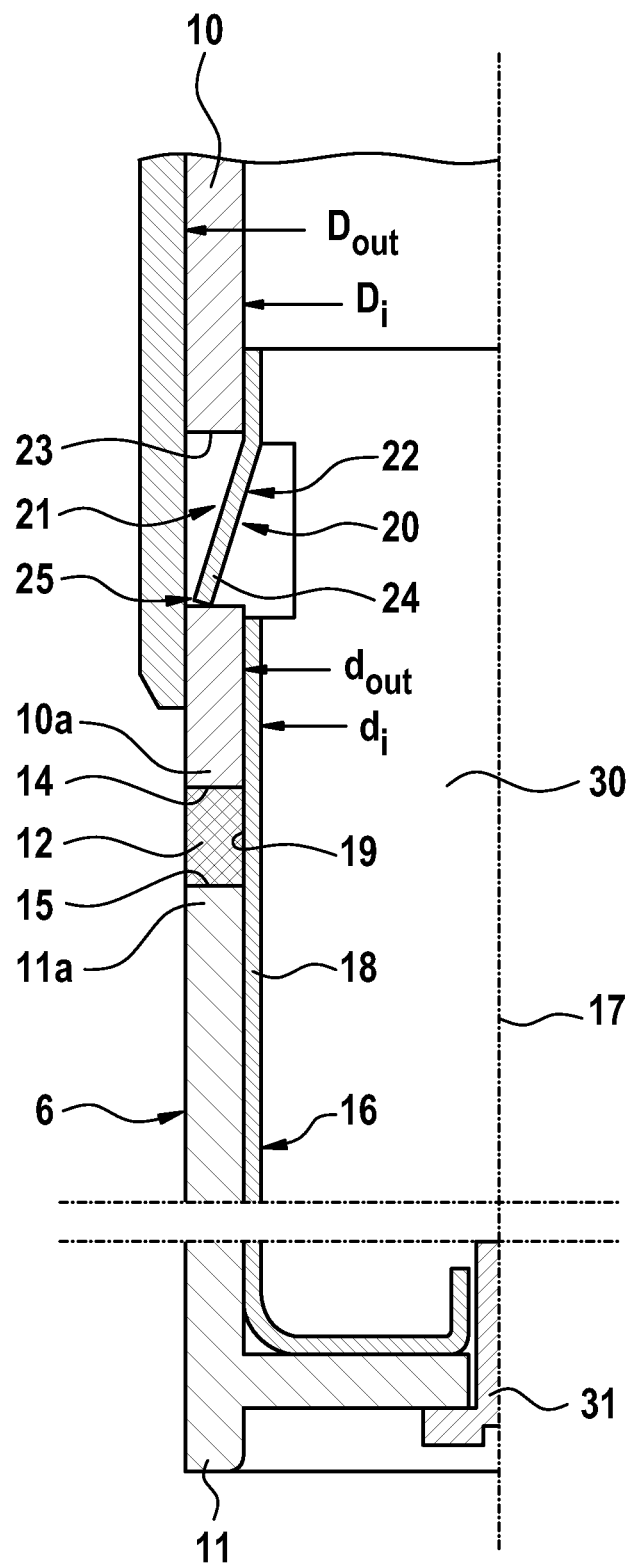
FIG. 2: a partial sectional view of the housing of the handle according to one or more embodiments illustrated and described herein, wherein an elastic sealing element is arranged between the end surfaces of the housing parts having substantially the same diameter, wherein the two housing parts are held together by a holding member positioned inside the housing.

As shown by FIG. 2, the end portions 10a, 11a of the housing parts 10, 11 to be connected to each other may have substantially the same diameter D with the end surfaces 14 and 15 having substantially the same contour and/or being substantially congruent with each other so that the end surfaces 14 and 15 can be positioned one onto the other when the housing parts 10 and 11 are brought together along common longitudinal axis 17. Due to the corresponding diameters and contours of the end portions 10a and 11a of the housing parts 10 and 11, the end portions 10 and 11 are not inserted one into the other as it is known from other toothbrush housings, but said end portions 10a and 11a form a butt joint or a jump joint without any significant step in the inner or outer circumferential surface at the interface 13 of the two housing parts 10 and 11.

More particularly, in the embodiment of FIG. 2 the end surfaces 14 and 15 of the end portions 10a and 11a of the housing parts 10 and 11 are not in direct contact with each other, but they butt against an annular or ring-shaped sealing element 12 which is sandwiched between the two end portions 10a and 11a. The sealing element 12 has substantially the same diameter and a contour substantially congruent with the contour of the end surfaces 14 and 15. Consequently, the interior space 30 defined by the inner circumference of the housing 6 has a substantially cylindrical shape in the zone of the interface 13 and the neighbouring end portions 10a and 11a of the housing parts 10 and 11. The inner circumference of the housing 6 which is formed by the inner circumference of the housing parts 10 and 11 and the inner circumference of the sealing element 12 is a continuous surface. Also the outer circumference of the housing 6 as formed by the housing parts 10 and 11 and sealing element 12 may form a continuous, smooth surface in the zone of the interface 13 and the neighbouring portions of the housing parts 10 and 11, since there is no difference in diameter. More particularly, the diameter D of the housing parts 10 and 11 at the end portions 10a and 11a thereof is basically the same at the inner circumference and at the outer circumference, i.e. the end portions 10a and 11a of the housing parts 10 and 11 have the same inner diameter $D_i$ and the same outer diameters $D_{out}$.

As can be seen from FIG. 2, the housing parts 10 and 11, at least at the end portions 10a and 11a may have basically the same wall thickness so that the housing 6 is given continuity over the interface 13 in terms of wall thickness and inner and outer circumferential surfaces.

As can be seen from FIG. 2, in one embodiment, the two housing parts 10 and 11 are held together by a holding member 16 extending along the inner circumference of the housing 6. More particularly, the holding member 16 is formed as a sleeve 18 and/or includes a sleeve portion which, with its outer circumferential surface, is in contact with the inner circumferential surface of the housing 6, wherein said sleeve 18 extends over the interface 13, for example, in FIG. 2.

On the one hand, the sleeve 18 or sleeve portion of the holding member 16 positions the housing parts 10 and 11 onto each other and aligns said housing parts 10 and 11 such that their longitudinal axes coincide. Such alignment is achieved by the form fit between the outer circumferential surface of the holding member 16, in particular the sleeve portion thereof, and the inner circumferential surface of the housing parts 10 and 11. The holding member 16 also supports the sealing element 12. More particularly, a portion of the sleeve 18 forms a support surface 19 supporting the inner circumferential surface 12a of the sealing element 12 to prevent said sealing element 12 from bulging inwardly.

On the other hand, the holding member 16 may form a tension element to apply axial tension to the housing parts 10 and 11 and to force the housing parts 10 and 11 together with the end surfaces 14 and 15 being pressed onto the sealing element 12. As can be seen from FIG. 2, the holding member 16 is axially fixed to the upper housing part 10 by means of form-fitting engagement means 20 and 21 provided at the holding member 16 and the inner circumferential surface of the housing part 10. More particularly, the holding member 16 can be locked to housing part 10 by means of an elastic latching element 22. In the shown embodiment of FIG. 2, the latching element 22 includes an elastic tongue 24 integrally formed in one piece with the sleeve 18 and separated therefrom by a U-shaped slot so that the elastic tongue 24 can project radially outwardly from the outer contour of the sleeve 18. Thus, the elastic tongue 24 forms an undercut projection 25 of the holding member 16. The elastic tongue 24 cooperates with an undercut recess 23 in the inner circumferential surface of the housing part 10. To bring the elastic tongue 24 in engagement with the recess 23, the sleeve 18 of the holding member 16 just needs to be inserted into the housing part 10 along the longitudinal axis 17 thereof. At the beginning of this linear insertion, the elastic tongue 24 is elastically deformed to flex inwardly so that the elastic tongue 24 slides over the inner circumferential surface of housing part 10. As soon as the elastic tongue 24 reaches the recess 23, the tongue 24 may elastically return to its projecting locking position where the tongue 24 extends into the recess 23 as shown by FIG. 2.

In one embodiment, the other housing part 11 is held at the holding member 16 by means of a tensioning element 31 applying axial tension to the second housing part 11. In the shown embodiment, the tensioning element 31 may be a bolt or a screw. The screw extends through a through-hole in the bottom of housing part 11 and is in screw engagement with an aligned recess in a bottom or radial flange portion of the holding member 16, for example, in FIG. 2. In one example, the tensioning axis of the tensioning element 31 extends substantially parallel to the longitudinal axis 17 of the housing 6 so that tightening the tensioning element 31 creates an axial tensioning force pressing the end surfaces 14 and 15 of the housing parts 10 and 11 against sealing element 12.

In the embodiment of FIG. 2, the holding member 16 is in particular made from a metal material such as steel, wherein the holding member 16 may have a wall thickness in the range from about 0.1 to about 0.7, in another embodiment, from about 0.3 to about 0.5 mm On the other hand, the housing parts 10 and 11 may be made from plastic, for example, in an injection molding process, wherein the housing parts 10 and 11 may have a wall thickness larger than the holding member 16. The wall thickness of the housing parts 10 and 11 may be in the range from about 150% to about 500%, and in another embodiment from about 200% to about 300% of the holding member wall thickness.

As can be seen from FIG. 2, the wall thickness in the zone of the interface 13 may be in the range of from about 0.7 mm to about 2.5 mm, and in another embodiment about 1.5 mm.

Figure 3:
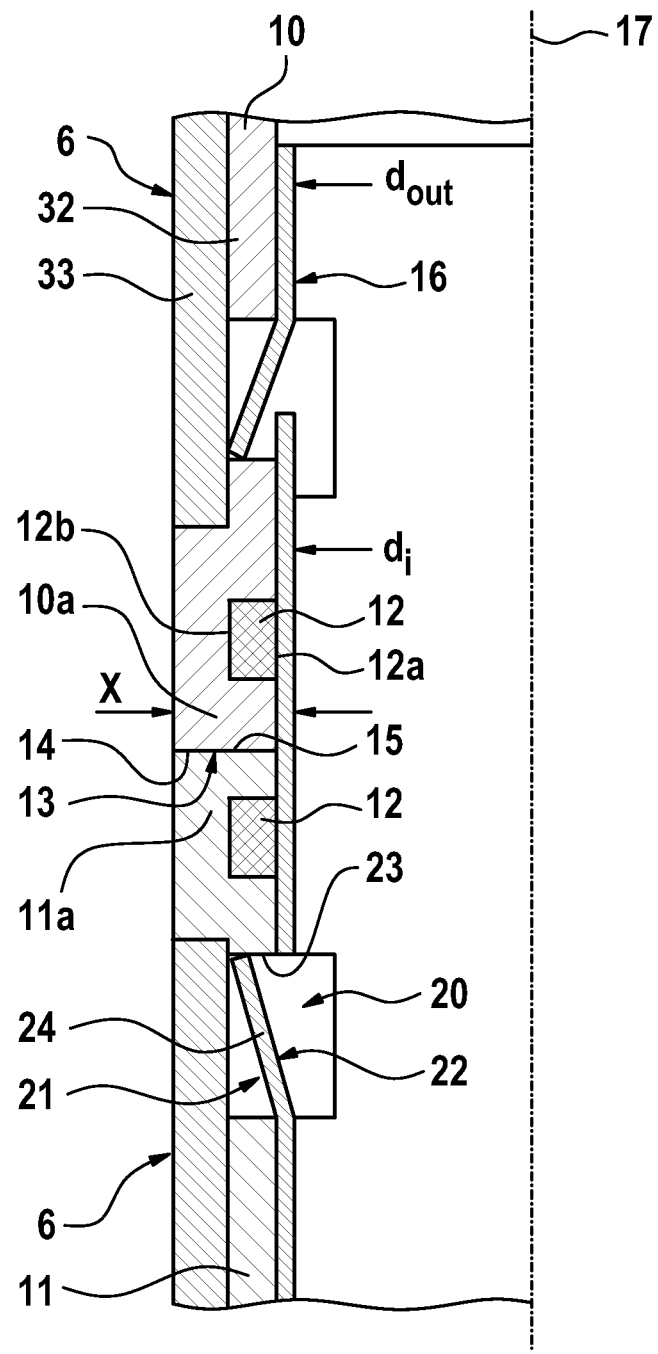
FIG. 3: a partial sectional view of the housing of the toothbrush of FIG. 1 according to one or more embodiments illustrated and described herein, wherein end surfaces of the housing parts directly contact each other and two sealing elements are in contact with a sleeve portion of the holding member to form a water-resistant seal for the interface between the housing parts.

FIG. 3 shows a further embodiment of the handle 2 which basically differs from the embodiment of FIG. 1 in the arrangement of the sealing element 12 and the locking of the holding member 16 to the second housing part 11. More particularly, as can be seen from FIG. 3, the sealing element 12 is not positioned between the end surfaces 14 and 15 of the housing parts 10 and 11, but a pair of sealing elements 12 are positioned on the inner circumferential side of the housing parts 10 and 11, wherein one sealing element 12 is associated with each of the housing parts 10 and 11.

The sealing elements 12 are spaced from each other in a direction of the longitudinal axis 17 and thus, the sealing elements 12 do not provide for direct sealing of the interface 13, but provide for water resistant sealing of the interface 13 in cooperation with the sleeve 18 of the holding member 16.

Each of the sealing elements 12 is an elastic, ring-shaped body positioned between the sleeve 18 of the holding member 16 and the respective housing part 10 or 11 at the circumference thereof. More particularly, in the shown embodiment the sealing elements 12 are received in an annular circumferential groove-shaped recess in the inner circumferential surface of the housing parts 10 and 11 so that the axial position of the sealing elements 12 in the direction of the longitudinal axis 17 is secured. The dimension and diameter of the sealing elements 12 and the depth of the groove-shaped recess in which the sealing elements 12 are received, are adapted such that an outer surface 12b of the sealing elements 12 is in sealing contact with the housing parts 10 and 11, whereas an inner surface 12a of the sealing elements 12 is in sealing contact with the outer circumferential surface of the sleeve 18. The sealing elements 12 are in particular made from an elastic material such as rubber and are formed such that they are pressed against the sleeve 18 as well as the housing parts 10 and 11. In one embodiment, the sealing elements 12 may be provided with inwardly projecting sealing lips having a diameter smaller than the inner diameter of the housing parts 10 and 11 so that the lips project inwardly from the groove-shaped recess. In addition or in the alternative, the sealing elements 12 may have outwardly projecting sealing lips in sealing engagement with the bottom of the groove-shaped recess in the housing parts 10 and 11.

Consequently, the pair of sealing elements 12 provide for sealing contacts of the sleeve 18 to the housing parts 10 and 11 on opposite sides of the interface 13 so that a water resistant seal is achieved via the sleeve 18 which extends over the interface 13 without having perforations or other through-holes to achieve water-resistant sealing.

In contrast to the embodiment of FIG. 2, the arrangement of the sealing elements 12 on the inner circumference of the housing parts 10 and 11 does not need any axial tensioning of the housing parts 10 and 11. Consequently, the holding member 16 may be adapted to just hold the housing parts 10 and 11 together.

As can be seen from FIG. 3, the holding member 16 may be locked to both housing parts 10 and 11 by means of a form-fitting engagement means 20 and 21 which basically corresponds to the embodiment of FIG. 2, so reference is given to the previous description in this regard.

In order to be able to unlock the housing parts 10 and 11, the housing parts 10 and 11 are adapted to provide access to the latching element 22 of the form-fitting engagement means 20 and 21. More particularly, the recess 23 in which the elastic tongue 24 extends in its locking position, is formed as a through-hole in a hard material layer, in particular hard plastic layer 32 of the respective housing part 10 or 11, wherein said through-hole is closed by a cover layer 33 made of a soft and/or deformable material such as soft plastic. Such deformable cover layer 33 allows to be deformed into the recess 23, thereby pushing the elastic tongue 24 radially inwards to get out of engagement with the recess 23 to unlock the respective housing part 10 or 11 from the holding member 16 and to allow separation of the housing parts by axial movement along the longitudinal axis 17.

In order to receive the sealing elements 12 in the aforementioned groove-shaped recesses in the housing parts 10 and 11, the wall thickness of the housing parts 10 and 11 may be larger than in the embodiment of FIG. 2. In one embodiment, the wall thickness of the end portions 10a and 11a of housing parts 10 and 11 may range from about 1.5 to about 3 mm, and in another embodiment from about 2.0 to about 2.3 mm However, such wall thickness may vary depending on the materials used and the design of the sealing elements 12.

Figure 4:
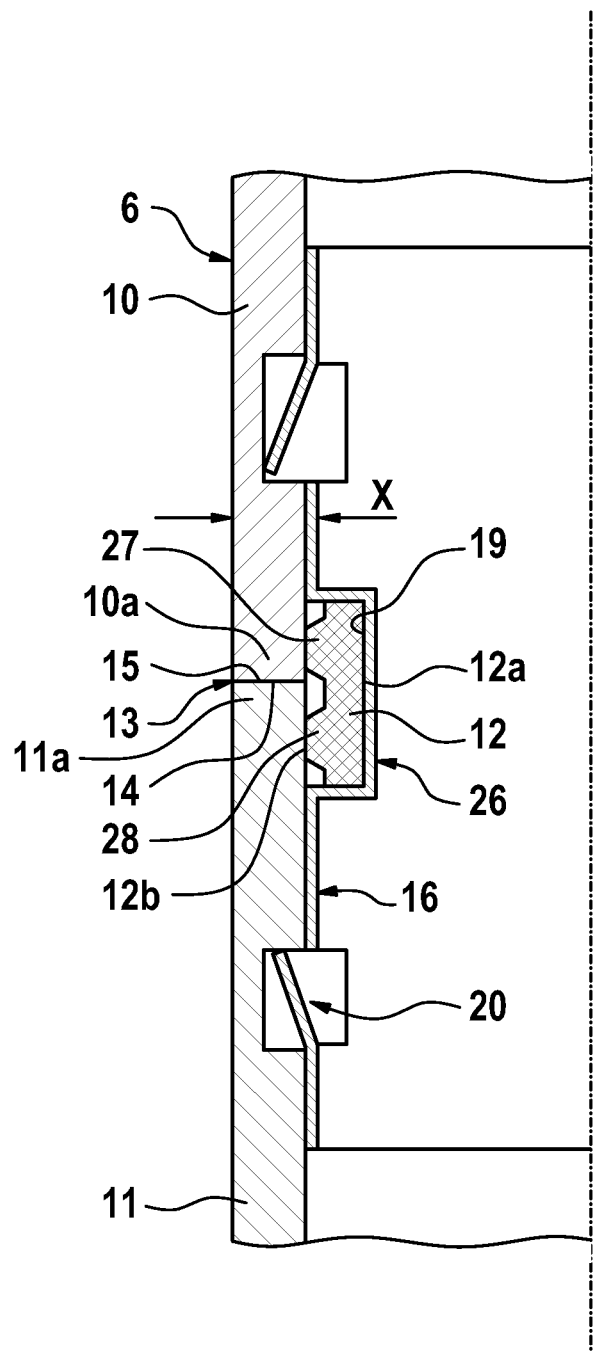
FIG. 4: a partial sectional view of the housing of the toothbrush of FIG. 1 according to one or more embodiments illustrated and described herein, wherein a sealing element is positioned on the inner circumferential surface of the housing and extends over the interface of the housing parts.

FIG. 4 shows another embodiment which differs from the embodiment of FIG. 3 in the provision, arrangement and positioning of the sealing element 12. More particularly, the sealing element 12 is not received in any recess in the housing parts 10 and 11, but is positioned just on the inner circumferential surfaces of the housing parts 10 and 11.

In order to accommodate the sealing element 12 between the circumferential surfaces of the housing 6 and the holding member 16, the holding member 16 is provided with an annular, groove-shaped recess 26 which is formed in the sleeve 18 or sleeve portion of the holding member 16. To form this recess 26, the wall of the sleeve 18 is formed with an inwardly projecting, ring-shaped bulge 34, thereby creating an annular space between the sleeve 18 and the housing 6 to accommodate the sealing element 12.

Furthermore, in contrast to the embodiment of FIG. 3, the sealing element 12 extends over the interface 13 and is in contact with both housing parts 10 and 11 at opposite sides of said interface 13. Thus, the sealing element 12 directly seals the interface 13.

In one embodiment, as shown by FIG. 4, the sealing element 12, at its outer circumferential surface, is provided with two radially outwardly projecting sealing lips one of which is in contact with a first one of the housing parts 10 and the other one is in contact with the second housing part 11. In one embodiment, the outer diameter 12d of the sealing element 12 is slightly larger than the outer diameter of the sleeve 18 and/or the inner diameter D, of the housing 6, when the sealing element 12 is in an undeformed condition. In other words, the sealing element 12 and the depth of the annular recess 26 in the sleeve 18 are adapted such that the sealing element 12 slightly projects radially outwards from the sleeve 18 when the sealing element 12 is not deformed, so as to achieve sealing pressure of the sealing element 12 onto the inner circumferential surface of the housing parts 10 and 11. For example, to balance a sufficient thickness of the sealing element 12 with minimum required space, the sealing element 12 may have a radial thickness in the range from about 2 to about 3 mm.

Figure 5:
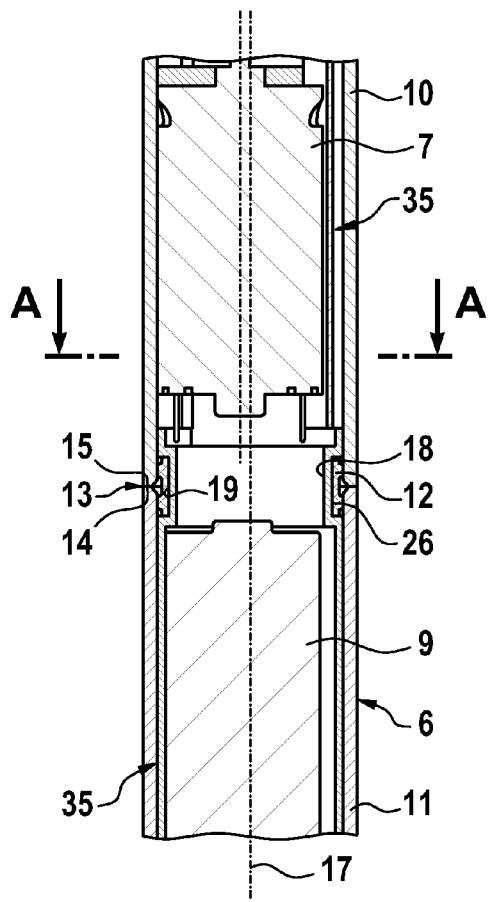
FIG. 5: a partial sectional view of the handle of the toothbrush of FIG. 1 according to one or more embodiments illustrated and described herein, wherein the interface between the housing parts and the sealing elements associated therewith is positioned between an electric motor and an accumulator received in the housing, wherein the holding member for holding together the housing parts is formed by the chassis supporting the electric motor and accumulator.
Figure 7:
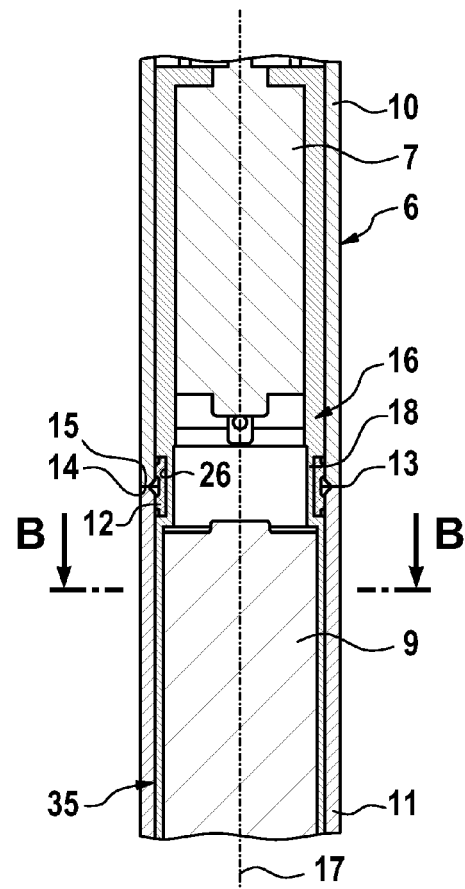
FIG. 7: is a partial sectional view of the handle in a plane perpendicular to the sectional plane shown in FIG. 5.

FIGS. 5 to 8 show an embodiment similar to FIG. 4, wherein FIGS. 5 and 7 show the interface 13 and the sealing element 12 positioned in a zone between the electric motor 7 and the accumulator of the power supply 9 which are received one behind the other in the housing 6 and spaced apart from each other by a certain distance in the direction of the longitudinal axis 17. In this space between the motor 7 and the accumulator of power supply 9, the sealing element 12 is positioned in contact with the inner circumference of the housing parts 10 and 11 neighboring the interface 13.

As can be seen by the embodiment shown in FIGS. 5 to 8, the holding member 16 also includes a sleeve 18 or sleeve portion where the sealing element 12 is accommodated. In addition to such sleeve portion, the holding member 16 may be formed as a part of the chassis for supporting and/or pre-mounting the functional components of the drive unit such as the motor 7 and the accumulator of the power supply 9. In one embodiment, the holding member 16 may be provided with support portions 35 and 37 extending along the inner circumferential surface of the housing parts 10 and 11 and forming a shell structure in which the electric motor and the accumulator of power supply 9 can be accommodated and supported. In addition to such components, the chassis by which holding member 16 is formed, may be provided with support portions for supporting further functional components such as the transmission and components of the control unit 8 such as the circuit board. As can be seen from FIG. 6, the circuit board of the control unit 8 may have a concave curvature to bow around the circumference of the electric motor 7 and/or to follow the cylindrical contour of the holding member 16 and/or chassis. In particular, the printed circuit board may be provided with grooves 36 extending parallel to longitudinal axis 17 to allow bending of the circuit board, wherein said grooves 36 are in particular provided on the side of the circuit board opposite to the metal side thereof. Providing the grooves 36 on the back side of the printed circuit board avoids damages to the electrical components when the circuit board is bent to follow the curvature of the housing 6 and/or the functional components such as motor 7 received inside said housing 6.

As can be seen from FIG. 6, the circuit board of control unit 8 is received within a gap or clearance space between the electric motor 7 and the housing 6. To provide for such circumferential gap, the chassis or holding member 16 is provided with a recess or window in which the control unit 8 can be positioned. In one embodiment, the chassis or holding member 16 may be formed to have two strip-shaped web portions 37 extending in parallel with longitudinal axis 17 along the circumferential surface of the housing part 10, wherein web portions 37 extend on opposite sides of the electric motor 7 to support said motor 7 therebetween. As can be seen from FIG. 6, the electric motor 7 may have flattened sides 38 which are in form-fitting engagement with flattened inner sides of said web portions 37 of the chassis. In a circumferential sector between said two strip-shaped web portion 37, the printed circuit board of control unit 8 is accommodated, for example, in FIG. 6.

In another embodiment, the holding member 16 or the chassis part thereof may form a shell-like support portion 35 for receiving the accumulator of the power supply 9. As can be seen from FIG. 8, this support portion 35 for the power supply 9 may form a slotted sleeve with an open cross-section extending over an angle β in the range from about 200° to about 300°.

In the embodiment according to FIGS. 5 to 8, the holding member 16 including the support portions 35 thereof and/or the chassis is in particular made from a plastic material, for example, a hard plastic which may be formed in an injection molding process. Making the chassis from plastic allows to easily provide portions of different wall thickness. For example, the strip-shaped web portions 37 for supporting the motor 7 may have a considerably thicker and/or varying wall thickness, for example, in FIG. 6.

Figure 9:
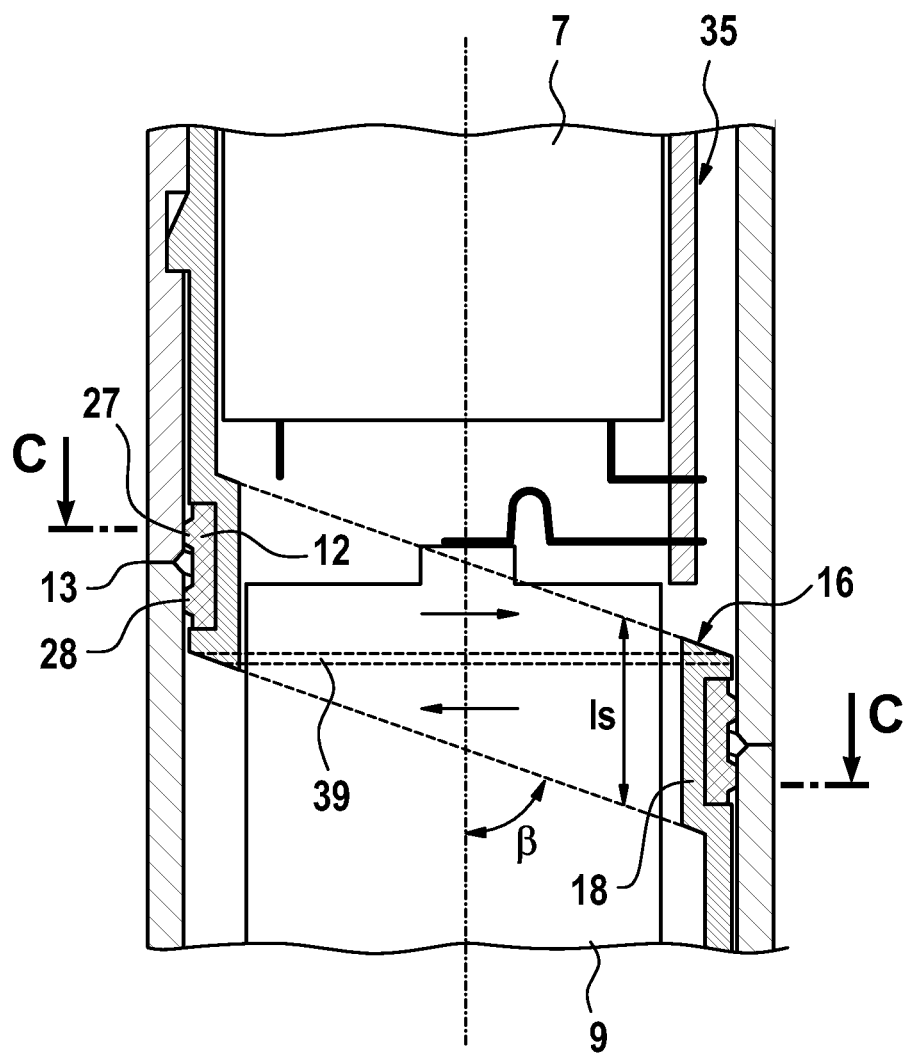
FIG. 9: a partial sectional view of the handle of the toothbrush of FIG. 1 according to one or more embodiments illustrated and described herein, wherein the interface between the two housing parts is provided in a plane tilted relative to the longitudinal axis of the handle at an acute angle and wherein the sealing element positioned on the inner circumferential surface of the housing follows the contour of the interface in the tilted plane.

FIGS. 9 and 10 show a further embodiment which is basically similar to the embodiment of FIGS. 5 to 8. The main difference to the embodiment of FIGS. 5 to 8 is the fact that the interface 13 between the housing parts 10 and 11 and consequently the ring-shaped sealing element 12 and the sleeve portion of the holding member 16 supporting the sealing element 12 extend in a plane 29 which is not perpendicular to the longitudinal axis 17 of the handle 2, but is tilted relative to said longitudinal axis 17 at an acute angle β which may range from about 60° to about 85°, in another embodiment, from about 60° to about 80°, and in another embodiment, about 70°. The tilting angle β may be adapted to the axial length ls of the sleeve 18 of holding member 16. More particularly, the tilting angle may be chosen such that the axial displacement of opposite sleeve portions in the direction of the longitudinal axis 17 substantially corresponds to the axial length ls or is greater than said axial length ls, wherein said opposite sleeve sections are assumed to be positioned in a sectional plane containing said longitudinal axis 17 and perpendicular to the tilting axis of tilting angle β. In other words, the sleeve sections of sleeve portion 18 defining the axial displacement are in the plane of FIG. 9 and represent the sleeve sections having the maximum axial displacement relative to each other. As can be seen from FIG. 9, it may be desirable to have the upper end of the sleeve portion 18 on one side thereof and the lower end of the sleeve portion 18 on the other side thereof on a line 39 perpendicular to the longitudinal axis 17. Such inclination of the plane of interface 13 allows for easy separation of the molding halves for molding the holding member 16 and/or the chassis and the sealing element 12 which may be formed in a two-step plastic molding process forming the sealing element 12 as a soft plastic portion integral and in one piece with a hard plastic body forming the holding member 16 and/or the chassis.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A handle of an electrical appliance for personal use comprising:
    an elongated housing for receiving functional components of the appliance; and
    a control unit or an electric power supply;
    wherein the housing includes at least two tube-shaped housing parts connected to each other at end portions thereof; wherein an annular sealing element is associated with the end portions to seal the interface between the housing parts;
    wherein the end portions of the housing parts have substantially the same diameter such that end surfaces of the housing parts abut against each other or against the annular sealing element without overlap; wherein a holding member extending over the interface between the housing parts and the sealing element is provided for holding the housing parts together; wherein the holding member is provided with form-fitting engagement means for engaging at least one of the housing parts at an inner circumferential side thereof and/or at least one of the housing parts is provided with form-fitting engagement means at its inner circumferential side to engage with the holding member; and wherein the form-fitting engagement means of the holding member and/or the housing parts include an elastic latching element adapted to elastically move in a direction transverse to the longitudinal axis of the housing when moving the holding member and the housing part relative to each other in the direction of the longitudinal axis, thus locking the holding member to the housing part, wherein the at least one housing part is provided with an undercut recess/projection at an inner circumferential surface thereof and the holding member is provided with an elastic tongue having an undercut projection/recess to lock with the recess/projection of the housing part when radially moving the elastic tongue.

2. The handle according to claim 1, wherein the holding member is adapted to form a tension member for tensioning the housing parts onto each other in a direction parallel to the longitudinal axis of the elongated housing.

3. The handle according to claim 1, wherein the holding member is formed by a sleeve insertable into the interior of the housing and/or having an outer circumference fitting onto the inner circumference of the housing.

4. The handle according to claim 1, wherein the holding member is formed by a chassis provided with support means for supporting at least one of the functional components received inside the housing, wherein the support means are formed in part by an inner circumferential surface of a sleeve portion of the holding member.

5. The handle according to claim 1, wherein the inner circumferential surfaces of the housing parts form together a continuous substantially cylindrical surface extending over the interface.

6. The handle according to claim 1, wherein the holding member is provided with an annular support surface for supporting an inner circumferential surface of the sealing element.

7. The handle according to claim 1, wherein the sealing element is positioned on the inner circumferential side of the housing and wherein an outer circumferential surface of the sealing element is in sealing contact with the inner circumferential surface of the housing.

8. The handle according to claim 1, wherein the holding member is provided with an annular, circumferential recess in which recess the sealing element is received, the sealing element having an outer diameter larger than the outer diameter of the holding member's portions neighbouring said annular circumferential recess.

9. The handle according to claim 1, wherein the sealing element extends over the interface between the housing parts and has two sealing portions one of which is in contact with a first one of the housing parts and the other one of which is in contact with a second one of the housing parts.

10. The handle according to claim 1, wherein a pair of sealing elements are provided for sealing the interface, wherein one of the sealing elements is in sealing contact to a first one of the housing parts and the holding member and the other one of the sealing elements is in sealing contact with a second one of the housing parts and the holding member, wherein the holding member's portion extending between the two sealing elements forms a watertight sleeve.

11. The handle according to claim 1, wherein the interface between the housing parts extends in a plane perpendicular to or tilted relative to the longitudinal axis of the housing at an angle of from about 60° to about 85° to the longitudinal axis.

12. An electric toothbrush comprising a handle according to claim 1.

* * * * *